(12) United States Patent
Yamagishi et al.

(10) Patent No.: US 6,861,847 B2
(45) Date of Patent: Mar. 1, 2005

(54) FERMENTATION CONTROLLER (75) Inventors: Junichi Yamagishi, c/o Unirec Co., Ltd., 6-3, 2-Chome, Kaminarimon, Taito-ku, Tokyo, 111-0034 (JP); Eikou Yo, Tokyo (JP)

(73) Assignees: Junichi Yamagishi, Tokyo (JP); Unirec Co., Ltd., Tokyo (JP)

( * ) Notice: Subject to any disclaimer, the term of this patent is extended or adjusted under 35 U.S.C. 154(b) by 0 days.

(21) Appl. No.: 10/393,899

(22) Filed: Mar. 21, 2003

(65) Prior Publication Data

US 2003/0184317 A1 Oct. 2, 2003

(30) Foreign Application Priority Data

Mar. 27, 2002 (JP) ........................................ 2002-087430

(51) Int. Cl.[7] ............................................... G01R 27/26
(52) U.S. Cl. ........................ 324/658; 324/663; 324/686
(58) Field of Search .............................. 324/663, 658, 324/686

(56) References Cited

U.S. PATENT DOCUMENTS

| 3,635,082 A | * | 1/1972 | Prellwitz et al. ......... 73/861.04 |
|---|---|---|---|
| 4,487,057 A | | 12/1984 | Lutz ........................... 73/40.5 |
| 4,965,206 A | * | 10/1990 | Kell ......................... 435/287.1 |
| 5,423,206 A | | 6/1995 | Hetzel ........................ 73/61.7 |
| 6,655,221 B1 | * | 12/2003 | Aspelund et al. ........ 73/861.04 |
| 2004/0183548 A1 | | 9/2004 | Yamagishi | |

FOREIGN PATENT DOCUMENTS

| JP | 08-256759 | 10/1996 |
|---|---|---|
| JP | 11-341947 | 12/1999 |

* cited by examiner

*Primary Examiner*—N. Le
*Assistant Examiner*—John Teresinski
(74) *Attorney, Agent, or Firm*—Jordan and Hamburg LLP (57) ABSTRACT

A fermentation controller correctly controls fermentation and produces a required material by fermentation. The fermentation controller (3) controls fermentation in a material production unit (1) that produces a material by fermentation. The controller (3) includes a capacitance sensor (63) to detect a capacitance change representative of a fermenting state in the material production unit and a memory (77) to store a reference capacitance change representative of a reference fermenting state. The controller compares the detected capacitance change with the reference capacitance change and controls fermentation in the material production unit according to the comparison result.

1 Claim, 8 Drawing Sheets

FERMENTATION CONTROLLER

BACKGROUND OF THE INVENTION

1. Field of the Invention

The present invention relates to a fermentation controller for controlling fermentation in a material production unit that produces a material such as sake (Japanese rice wine), beer, soy sauce, and the like by fermentation.

2. Description of the Related Art

Examples of fermentation controllers are disclosed in Japanese Patent Laid Open Publication Nos. 8-256759 and 11-341947.

The publication 8-256759 emits microwaves to a fermenting base material, measures an attenuation of transmitted microwaves, and controls fermentation accordingly to produce a fermented food. The publication 11-341947 measures the temperature and electrical conductivity of a fermenting liquid and controls the fermentation of the fermenting liquid.

These related arts control fermentation to provide objective materials.

The related art that emits microwaves affects fermentation by the radiated microwaves. The related art that measures an electrical conductivity affects fermentation due to corrosion of the conductivity measuring electrodes that are in contact with a fermenting liquid. None of the related arts, therefore, is able to correctly control fermentation.

SUMMARY OF THE INVENTION

An object of the present invention is to provide a fermentation controller capable of correctly controlling fermentation and providing an objective material.

A first aspect of the present invention provides a fermentation controller for controlling fermentation in a material production unit that produces a material by fermentation. The fermentation controller includes a capacitance sensor to detect a capacitance change representative of a fermenting state in the material production unit and a storage unit to store a reference capacitance change representative of a reference fermenting state. The fermentation controller compares the detected capacitance change with the reference capacitance change and controls fermentation in the material production unit according to the comparison result.

For the fermentation controller of the first aspect, a second aspect of the present invention provides the capacitance censor with a measuring electrode and a ground electrode each made of conductive metal foil. The electrodes are insulated from a passage through which the fermenting material in the material production unit travels, and the electrodes are wound around the passage.

For the fermentation controller of the second aspect, a third aspect of the present invention forms the ground electrode narrower than the measuring electrode and alternately arranges the ground electrode and measuring electrode.

For the fermentation controller of any one of the second and third aspects, a fourth aspect of the present invention spirally winds the measuring electrode and ground electrode around the passage in the material traveling direction.

The first aspect controls fermentation in the material production unit according to a fermenting state and produces a material. To control fermentation, the first aspect employs the capacitance sensor to detect a capacitance change representative of a fermenting state in the material production unit, compares the detected capacitance change with the reference capacitance change stored in the storage unit. With this control, the material production unit can properly produce a required material.

Detecting a capacitance change to control fermentation according to the first aspect never affects the fermentation, and therefore, can correctly produce the required material by fermentation.

In addition to the effects of the first aspect, the second aspect forms the capacitance sensor from the measuring electrode and ground electrode each made of conductive metal foil. The electrodes are insulated from the passage through which a material being produced in the material production unit travels, and the electrodes are wound around the passage. The second aspect correctly detects a capacitance change on the material moving through the passage and surely controls fermentation in the material production unit.

In addition to the effects of the second aspect, the third aspect forms the ground electrode narrower than the measuring electrode and alternately arranges the ground electrode and measuring electrode. The third aspect correctly detects a capacitance change on the material moving through the passage and surely controls fermentation in the material production unit.

In addition to the effects of the third aspect, the fourth aspect spirally winds the measuring electrode and ground electrode around the passage in the material flowing direction. The fourth aspect correctly detects a capacitance change on the material moving through the passage and surely controls fermentation in the material production unit.

DETAILED DESCRIPTION OF EMBODIMENTS

First Embodiment

Figure 1:
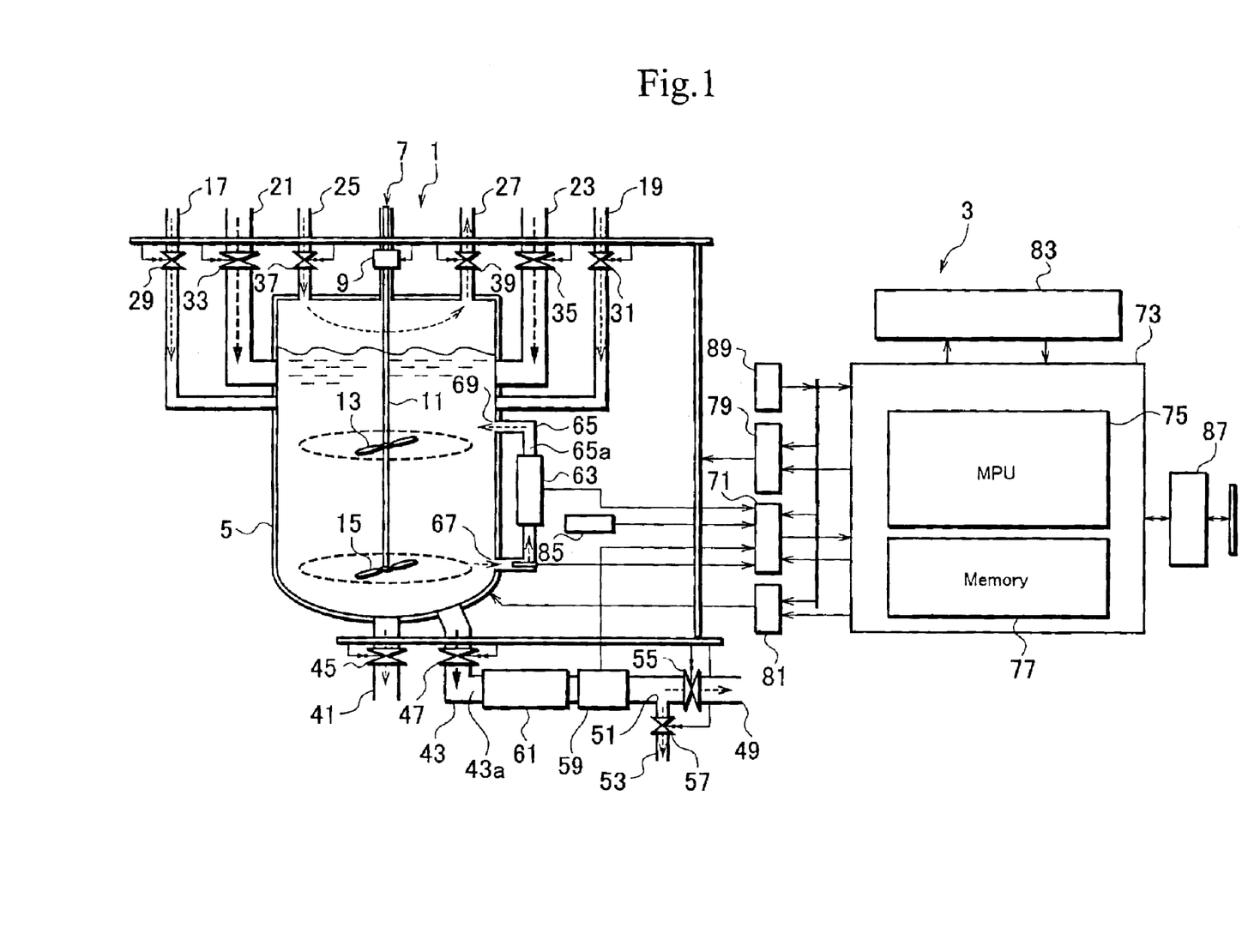
FIG. 1 is a schematic view showing a fermentation controller for controlling fermentation in a material production unit that produces a material by fermentation, according to a first embodiment of the present invention.

FIG. 1 schematically shows a fermentation controller 3 for controlling fermentation in a material production unit 1 that produces a material by fermentation, according to the first embodiment of the present invention. The material produced in the material production unit 1 is, for example, sake (Japanese rice wine).

The material production unit 1 has a fermenting tank 5. The internal temperature of the fermenting tank 5 is electrically controllable. The fermenting tank 5 has a stirrer 7. The stirrer 7 has a rotary shaft 11 driven by a motor 9. The shaft 11 has two vanes 13 and 15 arranged at upper and lower parts of the shaft 11.

The top of the fermenting tank 5 has a cultured-ferment supply bypass pipe 657, an alcohol supply bypass pipe 659, a steamed-rice supply pipe 21, a water supply pipe 23, an air supply pipe 25, and an air discharge pipe 27. The bypass pipe 657 has a first solenoid valve 29, the bypass pipe 659 has a second solenoid valve 31, the pipe 21 has a third solenoid valve 33, the pipe 23 has a fourth solenoid valve 35, the pipe 25 has a fifth solenoid valve 37, and the pipe 27 has a sixth solenoid valve 39.

The bottom of the fermenting tank 5 has a sake-lees discharge pipe 41 and a sake outlet pipe 43. The pipe 41 has a seventh solenoid valve 45, and the pipe 43 has an eighth solenoid valve 47.

The outlet pipe 43 is made of an insulator such as resin, for example, vinyl chloride. The outlet pipe 43 may be made of the insulator only at a part where a first sensor 59 is arranged. The insulator may be quartz glass. An end of the outlet pipe 43 has an outlet 49. In the vicinity of the outlet 49, there is a branch mouth 51 connected to a branch pipe 53. The branch pipe 53 is connected to a collection tank (not shown) used to collect sake containing fine foreign matter.

The outlet 49 has a ninth solenoid valve 55, and the branch pipe 53 has a tenth solenoid valve 57. The valves 55 and 57 serve as adjusters to switch a flow of sake to one of the outlet 49 and branch mouth 51.

If the ninth solenoid valve 55 is opened, the outlet 49 discharges sake of good quality containing no foreign matter. If the valve 55 is closed, the discharging of sake from the outlet 49 is stopped. If the tenth solenoid valve 57 is opened with the ninth solenoid valve 55 closed, sake containing fine foreign matter is discharged from a passage 43a in the outlet pipe 43 to the branch pipe 53 from where to the collection tank.

The outlet pipe 43 has the first sensor 59, which is a capacitance sensor to detect a capacitance on the passage 43a. The first sensor 59 is arranged upstream of the branch mouth 51.

Upstream of the first sensor 59, there is a filter 61 to remove foreign matter from sake flowing through the passage 43a.

The material production unit 1 has a second sensor 63, which is a capacitance sensor to detect a capacitance change representative of a fermenting state in the material production unit 1. The second sensor 63 is attached to a bypass pipe 65. The bypass pipe 65 is made of an insulator such as resin, for example, vinyl chloride. The bypass pipe 65 may be made of the insulator only at a part where the second sensor 63 is arranged. The insulator may be quartz glass.

The bypass pipe 65 is connected to a sample inlet 67 formed at the bottom of the fermenting tank 5 and a sample outlet 69 formed at an intermediate part of the fermenting tank 5. The sample inlet 67 faces the vane 15. When the vane 15 is rotated, the contents of the fermenting tank 5 enter the sample inlet 67, flow through a passage 65a in the bypass pipe 65, pass through the second sensor 63, and exit from the sample outlet 69 into the fermenting tank 5.

Signals from the first and second sensors 59 and 63 are sent through a signal processor 71 to a control unit 73. The control unit 73 receives reference capacitance changes through the signal processor 71.

The reference capacitance changes may include a no-foreign-matter capacitance change representative of sake containing no foreign matter and a production reference capacitance change representative of a reference fermenting state in the material production unit 1. The production reference capacitance change indicates a proper shipment time of sake of good quality. The details of this will be explained later.

The control unit 73 includes, for example, an MPU (microprocessor unit) 75 and a memory 77. In place of the MPU 75, a DSP (digital signal processor) is employable. The memory 77 serves as a storage unit to store the reference capacitance changes including the no-foreign-matter capacitance change and production reference capacitance change. The control unit 73 compares a detected capacitance change with the production reference capacitance change, and according to the comparison result, controls fermentation in the material production unit 1.

More precisely, the control unit 73 compares a capacitance change detected by the second sensor 63 with the production reference capacitance change, controls the fermenting state of the material flowing through the passage 65a, and determines whether or not the material is suitable for shipment.

The control unit 73 also compares a capacitance change detected by the first sensor 59 with the no-foreign-matter capacitance change, and according to the comparison result, measures a quantity of fine foreign matter contained in sake flowing through the passage 43a.

The control unit 73 is connected through a driver 79 to the first to tenth solenoid valves 29, 31, 33, 35, 37, 39, 45, 47, 55, and 57.

The control unit 73 is also connected to a temperature controller 81 to electrically control the internal temperature of the fermenting tank 5, a display panel 83, an ambient sensor 85, a data transfer interface 87, and a power source 89. The ambient sensor 85 detects temperature, humidity, and the like around the fermenting tank 5 and is connected through the signal processor 71 to the control unit 73.

Figure 2:
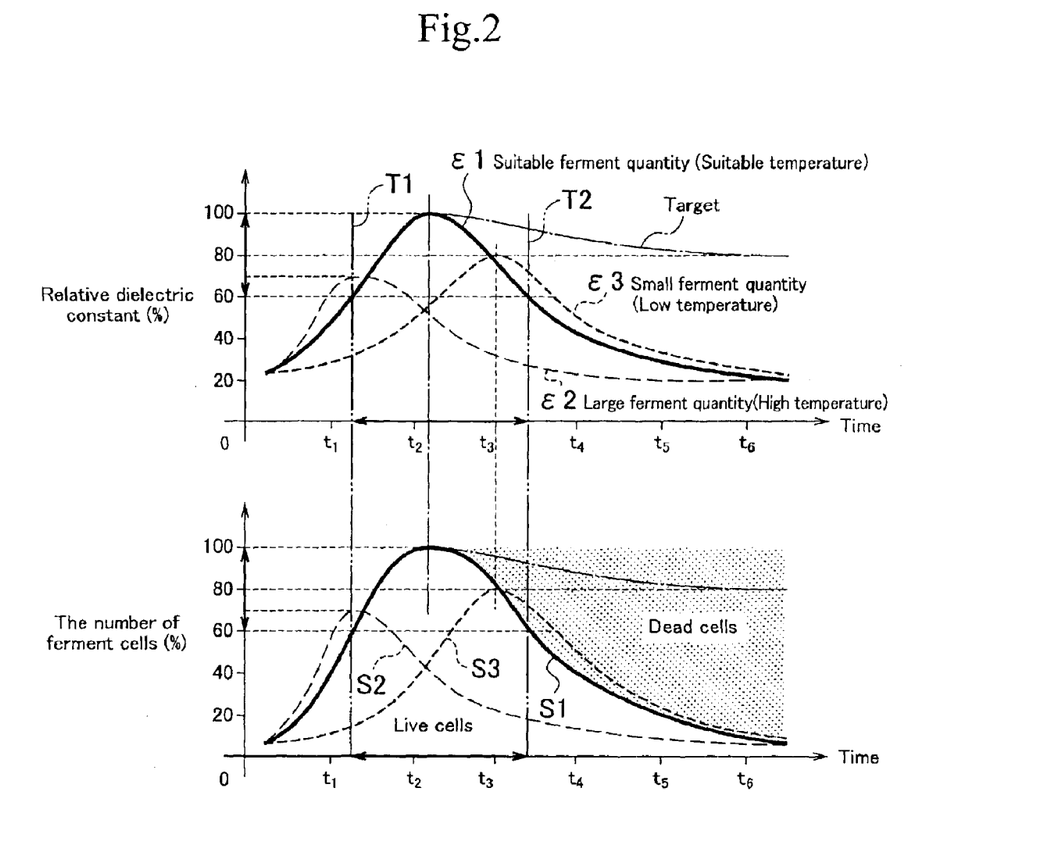
FIG. 2 shows graphs indicating reference capacitance changes representative of reference fermenting states according to the first embodiment.

FIG. 2 shows reference capacitance changes (production reference capacitance changes) related to fermentation. These types of capacitance changes are already known and are disclosed in scientific literatures. A lower graph of FIG. 2 shows temporal changes in the number of ferment cells during fermentation, and an upper graph of FIG. 2 shows temporal capacitance changes corresponding to the ferment cell changes. The capacitance changes are represented with relative dielectric constants with an optimum one being 100%.

In FIG. 2, a curve S1 indicates temporal changes in the number of ferment cells that is appropriate for a fermentation base material, a curve S2 indicates temporal changes in the number of ferment cells that is large for a fermentation base material, and a curve S3 indicates temporal changes in the number of ferment cells that is small for a fermentation base material. A curve $\epsilon1$ indicates capacitance changes corresponding to the curve S1, a curve $\epsilon2$ capacitance changes corresponding to the curve S2, and $\epsilon3$ capacitance changes corresponding to the curve S3.

As is apparent in FIG. 2, a proper shipping time for sake of good quality is when the number of ferment cells reaches 60% or higher of the highest value. The first embodiment controls fermentation according to the capacitance changes shown in the upper graph of FIG. 2. In FIG. 2, T1 is a shipment possible time and T2 is a best-before date. If a detected capacitance change falls between T1 and T2, sake of good quality can be shipped. Accordingly, the capacitance changes along the curve ∈1 are stored as the production reference capacitance changes and are used to determine a proper shipment time, or to determine if a relative dielectric constant is 60% or higher. It is possible to store the capacitance changes of the curves ∈2 and ∈3 in the memory 77, to control fermentation depending on the quantities of ferment cells.

Figure 3:
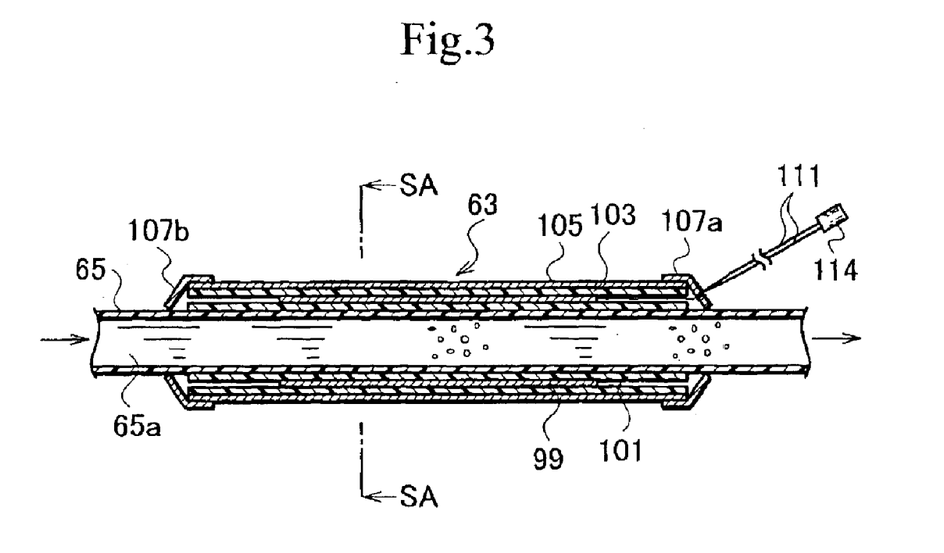
FIG. 3 is a sectional view showing a sensor of the fermentation controller and the periphery thereof according to the first embodiment.
Figure 4:
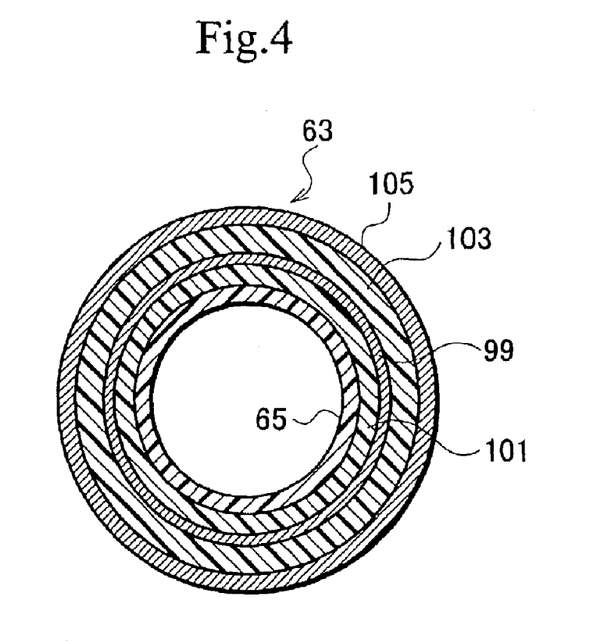
FIG. 4 is an enlarged sectional view taken along a line SA—SA of FIG. 3.
Figure 5:
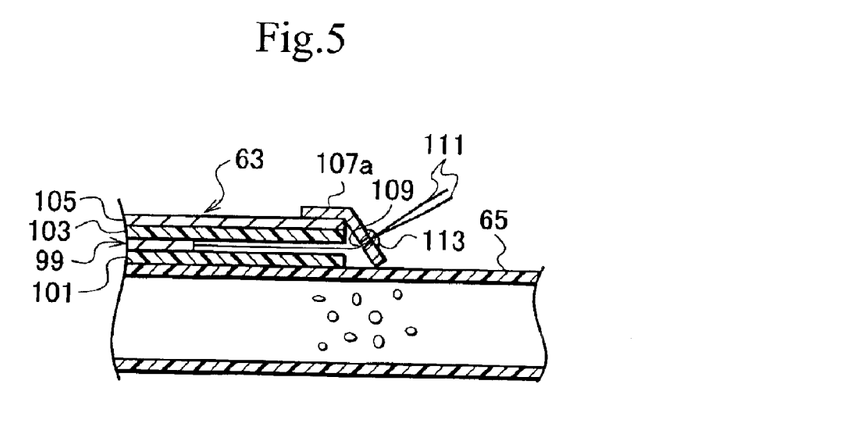
FIG. 5 is an enlarged sectional view showing a part of the sensor of FIG. 3.

FIGS. 3 to 5 show an example of one of the first and second sensors 59 and 63.

FIG. 3 is a sectional view showing one of the sensors 59 and 63 and the periphery thereof, FIG. 4 is an enlarged sectional view taken along a line SA—SA of FIG. 3, and FIG. 5 is an enlarged sectional view showing a part of FIG. 3. The first and second sensors 59 and 63 have an identical structure, and therefore, the second sensor 63 will be explained. Only difference between the sensors 59 and 63 is that the first sensor 59 is arranged on the outlet pipe 43 and the second sensor 63 is arranged on the bypass pipe 65.

In FIGS. 3 to 5, the second sensor 63 is a capacitance sensor and consists of an electrode 99 made of conductive metal foil. The electrode 99 is insulated from the passage 65a and is wound around the same. The electrode 99 consists of a measuring electrode 115 and a ground electrode 117.

The electrode 99 is wound around a cylinder 101 that is attached around the bypass pipe 65. According to the first embodiment, the cylinder 101 is made of an insulator such as vinyl chloride. The insulator may be any other insulator such as glass and resin. The cylinder 101 is tightly fitted around the bypass pipe 65. The cylinder 101 may be tightly attached around the bypass pipe 65 by, for example, bonding. With the cylinder 101, the second sensor 63 can be made as an assembly that is easily integrated with the bypass pipe 65. According to the first embodiment, the bypass pipe 65 is made of an insulator such as vinyl chloride at a part where the second sensor 63 is attached. The bypass pipe 65 may entirely be made of the insulator. The relationship between the second sensor 63 and the bypass pipe 65 is the same as that between the first sensor 59 and the outlet pipe 43.

The electrode 99 is made of conductive metal foil. The electrode 99 is covered with an insulator 103, which is covered with a shield 105. According to the first embodiment, the insulator 103 is a vinyl-chloride pipe covering the electrode 99. The insulator 103 may be made of resin, quartz glass, or the like.

According to the first embodiment, the shield 105 is an aluminum pipe tightly fitted around the insulator 103. End shields 107a and 107b are fixed to both ends of the shield 105. According to the first embodiment, the end shields 107a and 107b are made of aluminum.

Figure 6:
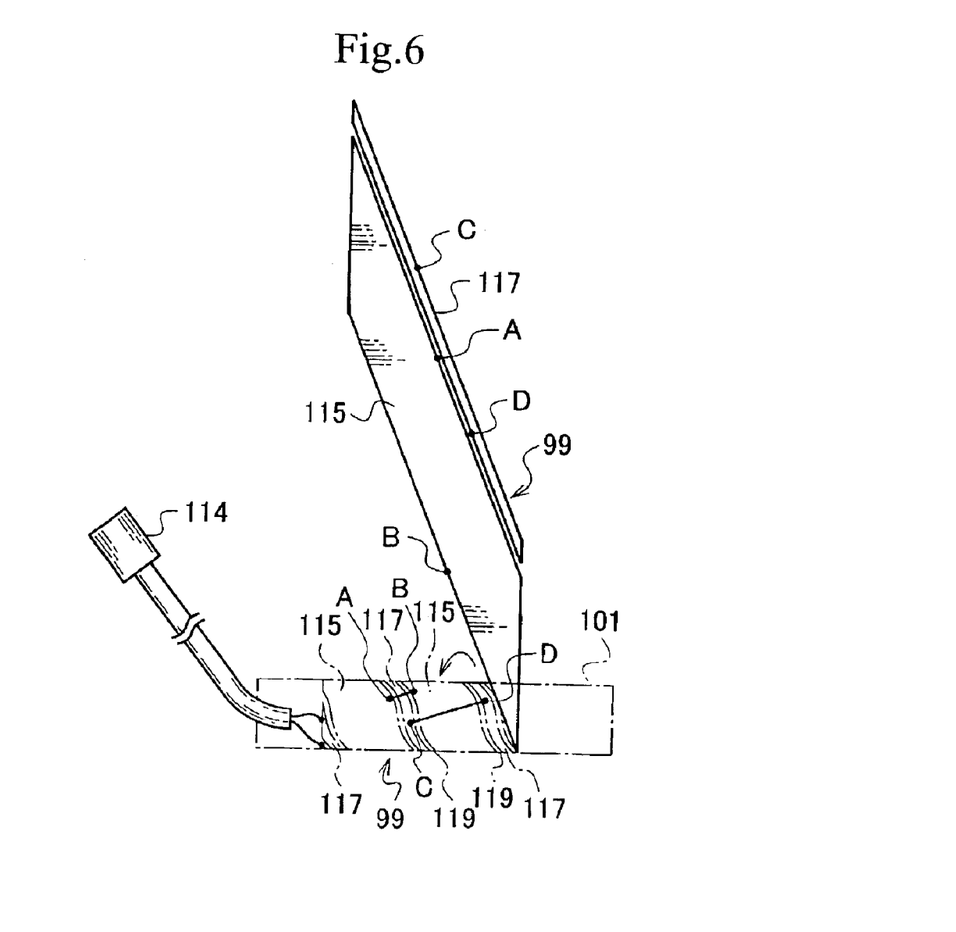
FIG. 6 is an explanatory view showing a winding state of electrodes of the sensor of FIG. 3.

In FIG. 5, the end shield 107a has a through hole 109 to pass leads 111 of the electrode 99 to the outside. Between the end shield 107a and the leads 111, resin 113 is applied. In FIGS. 3 and 6, the leads 111 are connected to a connector 114.

FIG. 6 shows an example of the structure of the electrode 99. As indicated with dash-and-dot lines, the electrode 99 is spirally wound around the cylinder 101. Continuous lines in FIG. 6A indicate a developed state of the electrode 99. The electrode 99 consists of the measuring electrode 115 and ground electrode 117. In the developed state, the electrodes 115 and 117 are each a parallelogram ribbon made of copper foil. The lengths of short sides (vertical edges depicted with the continuous lines in FIG. 6) of the electrodes 115 and 117 plus the length of a gap 119 between the electrodes 115 and 117 are substantially equal to a circumferential length of the cylinder 101.

The ground electrode 117 is narrower than the measuring electrode 115. The measuring electrode 115 and ground electrode 117 are spirally wound around the cylinder 101 in a fluid flowing direction as indicated with the dash-and-dot lines. The electrodes 115 and 117 are fixed to the cylinder 101 by, for example, bonding. The number of windings of the electrodes 115 and 117 around the cylinder 101 is, for example, three. The number of windings, however, is optional as long as the electrodes 115 and 117 can properly detect capacitance along the bypass pipe 65. Between the electrodes 115 and 117 around the cylinder 101, there is the gap 119.

Around the cylinder 101, the electrodes 115 and 117 are alternately arranged. In the wound state, the adjacent windings of the measuring electrode 115 are short-circuited between points A and B. Similarly, the adjacent windings of the ground electrode 117 are short-circuited between points C and D. In FIG. 6, the short-circuited points A, B, C, and D are on the same plane for the sake of easy understanding. In practice, the points A, B, C, and D are located as shown in the developed view of FIG. 6.

Figure 7:
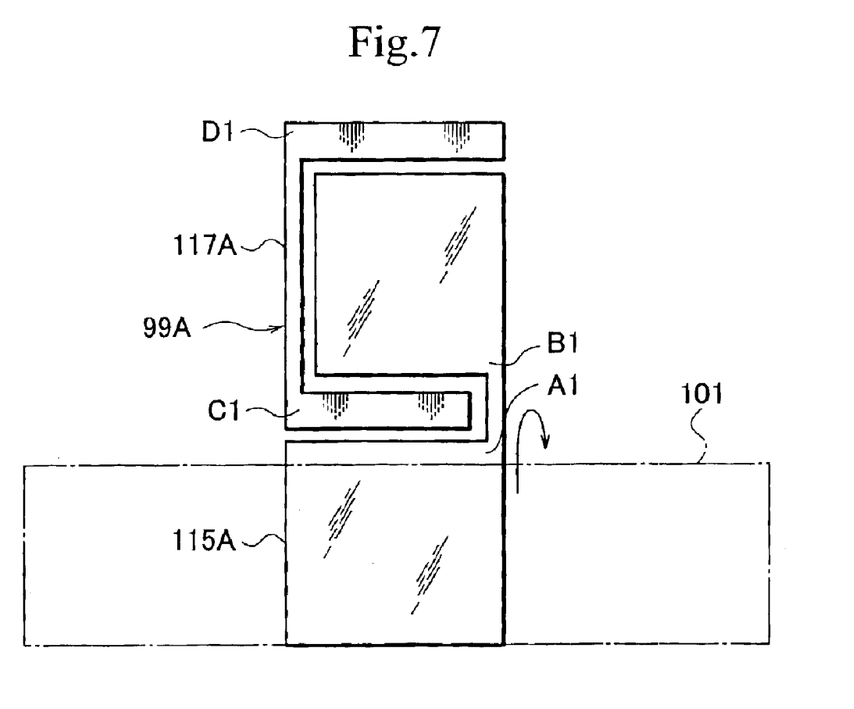
FIG. 7 is an explanatory view showing developed electrodes corresponding to the electrodes of FIG. 6.

FIG. 7 shows the structure of an electrode 99A, which is an equivalent of the electrode 99. The short-circuit points A, B, C, and D of the electrode 99 of FIG. 6 positionally correspond to points A1, B1, C1, and D1 of the electrode 99A of FIG. 7. With the parallelogram electrodes 115 and 117 and short-circuit points A, B, C, and D, the electrode 99 can spirally be wound around the cylinder 101.

In place of the electrode 99 of FIG. 6, the electrode 99A of FIG. 7 is employable. In FIG. 7, the electrode 99A consists of a measuring electrode 115A and a ground electrode 117A and can be wound around the cylinder 101. The electrode 99 of FIG. 6 that is spirally wound around the cylinder 101 can more correctly and easily detect a capacitance change on the passage 65a than the electrode 99A of FIG. 7.

Figure 8:
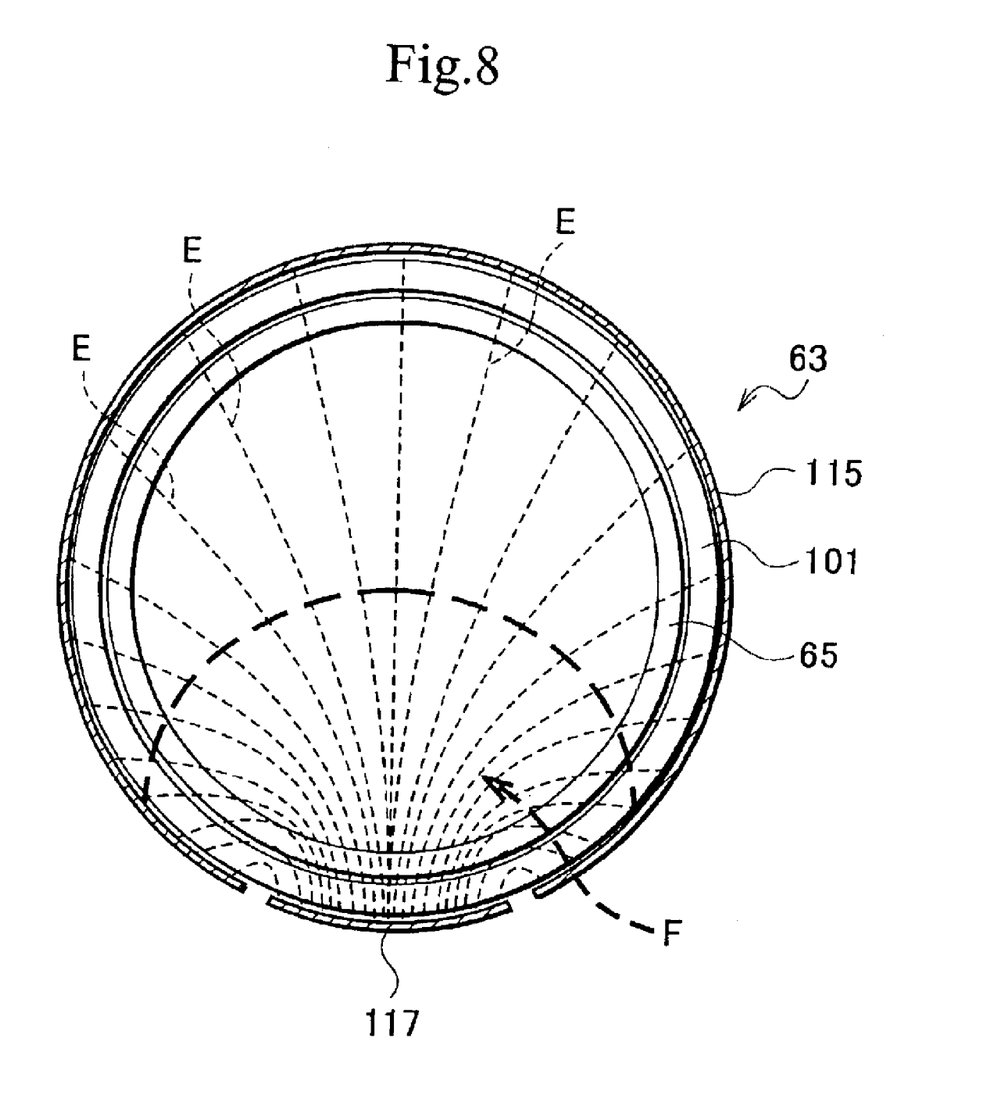
FIG. 8 is a schematic sectional view of the pipe with a ground electrode and measuring electrode of the sensor of FIG. 3.

FIG. 8 is a schematic sectional view of the bypass pipe 65 with a ground electrode 117 and measuring electrode 115 of the sensor 63 of FIG. 3. In FIG. 8, the insulator 103 and the shield 105 are not shown. The first and second sensors 59 and 63 have an identical structure mentioned above, and therefore, the second sensor 63 will be explained. According to the sensor 63 serving as a capacitance sensor, the ground electrode 117 is narrower than the measuring electrode 115. Therefore, if the ground electrode 117 was positioned near the lower portion of the bypass pipe 65, sensitivity-curved lines E forms a high sensitivity area F for the sensitivity-curved lines E in the lower portion of the bypass pipe 65 adjacent to the ground electrode 117. Thus, when the ground electrode 117 and measuring electrode 115 are alternately disposed and are wound to be spiral along a flow direction, the high sensitivity area F is distributed around the circumference of the bypass pipe 65 and formed in a 360 degree range. Accordingly, the sensor 63 can accurately make detection of capacitance of the bypass pipe 65 with the high sensitivity area F formed in the 360 degree range.

Furthermore, a capacitance sensor with a ground electrode and measuring electrode having similar widths will have a relatively larger capacitance than the sensor 63 with the measuring electrode 115 of width substantially larger than the width of the ground electrode 117. As a result, the capacitance sensor with a ground electrode and measuring electrode having similar widths has a greater sensitivity to noise than the sensor 63 with the measuring electrode 115 of width substantially larger than the width of the ground electrode 117. Thus, the sensor 63 can make detection with greater accuracy.

Figure 9:
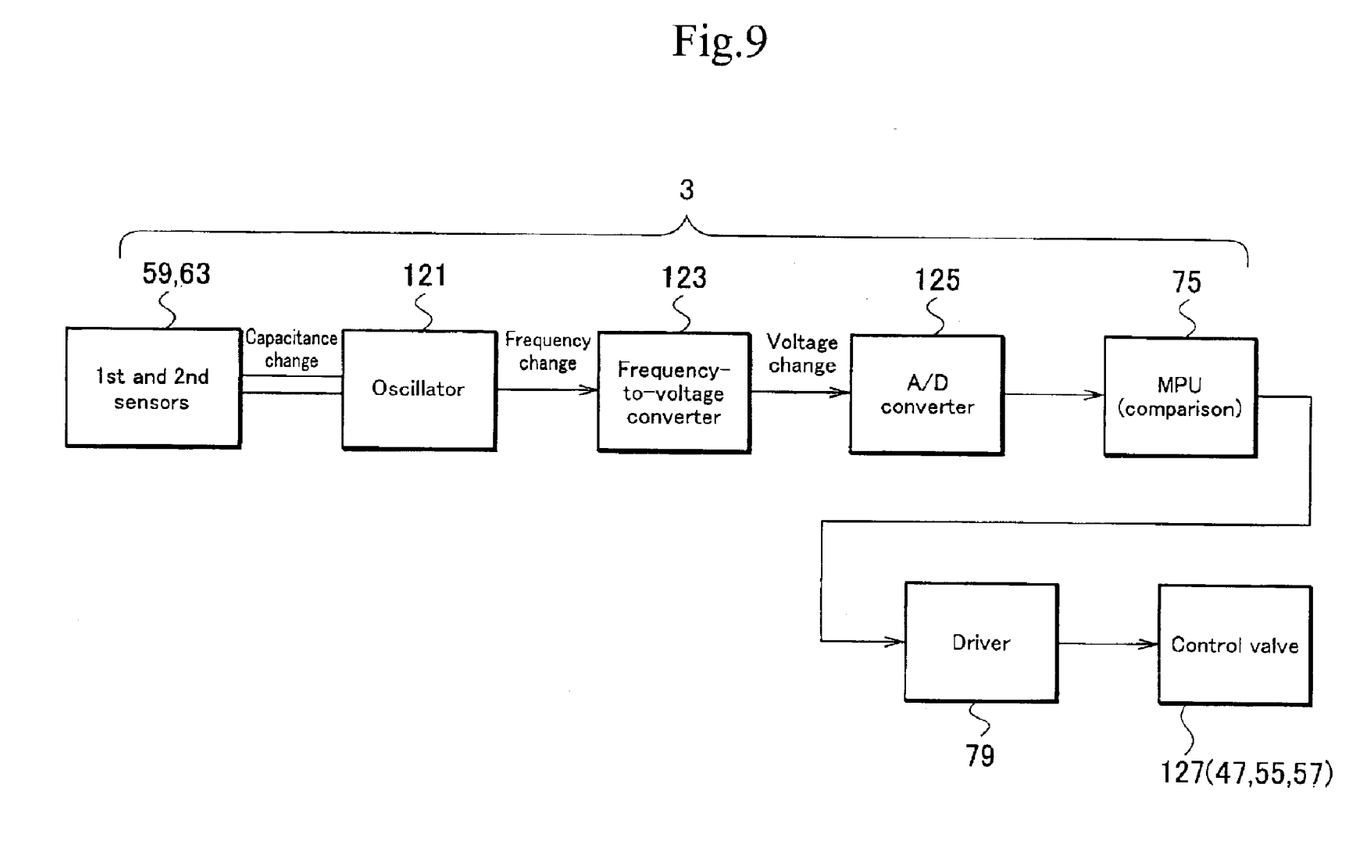
FIG. 9 is a block diagram showing the fermentation controller according to the first embodiment.

FIG. 9 is a block diagram schematically showing the fermentation controller 3 according to the first embodiment. The sensors 59 and 63, an oscillator 121, a frequency-to-voltage converter 123, an A/D converter 125, and the MPU 75 form the fermentation controller 3. A control valve 127 in FIG. 9 collectively represents the eighth, ninth, and tenth solenoid valves 47, 55, and 57 of FIG. 1.

A capacitance change detected by any one of the first and second sensors 59 and 63 is transferred to the oscillator 121, which provides a frequency change representative of the capacitance change. The frequency change is converted by the frequency-to-voltage converter 123 into a voltage. The voltage is converted by the A/D converter 125 into a digital binary signal. According to the digital binary signal, the MPU 75 compares the detected capacitance change with the reference capacitance changes.

According to a comparison result based on a detected signal from the first sensor 59, the MPU 75 measures the quantity of fine foreign matter contained in sake flowing through the passage 43a. According to a comparison result based on a detected signal from the second sensor 63, the MPU 75 measures a fermenting state in the fermenting tank 5 and determines whether or not sake is appropriate for shipment.

The control unit 73 properly opens and closes the first to sixth solenoid valves 29, 31, 33, 35, 37, and 39 shown in FIG. 1, to feed steamed rice, water, ferments, and alcohol into the fermenting tank 5 and supply air to an upper part of the fermenting tank 5 to keep the ferments alive. The control unit 73 drives the motor 9 to rotate the shaft 111 with the vanes 13 and 15.

Under these conditions, the contents of the fermenting tank 5 produce sake by fermentation. At this time, the ambient sensor 85 detects a temperature and humidity around the fermenting tank 5 and transfers the detected values to the control unit 73. According to the detected temperature and humidity, the control unit 73 controls the temperature controller 81 to control the internal temperature of the fermenting tank 5. The ambient temperature and internal temperature of the fermenting tank 5 may be displayed on the display panel 83.

The quality of sake can be improved by correctly controlling fermentation in the fermenting tank 5. A stirring action by the vane 15 sends the contents of the fermenting tank 5 into the sample entrance 67. The contents then pass through the bypass pipe 65 and second sensor 63, which detects a capacitance change on the passage 65a where the contents are traveling.

The control unit 73 compares the detected capacitance change with the production reference capacitance changes and determines an appropriate shipping time. The determined shipping time may be displayed on the display panel 83. If the MPU 75 of the control unit 73 determines that it is the shipping time T1 (FIG. 2), the MPU 75 controls the driver 79 to open the eighth solenoid valve 47 to guide sake from the fermenting tank 5 to the outlet pipe 43.

In the outlet pipe 43, the sake flows through the passage 43a up to the outlet 49. At this time, the first sensor 59 detects a capacitance change on the passage 43a.

If the control unit 73 detects at the first sensor 59 fine foreign matter in the sake, the MPU 75 controls the driver 79 to close the ninth solenoid valve 55 and open the tenth solenoid valve 57. As a result, the sake containing fine foreign matter is passed through the branch pipe 53 to the collection tank.

If no foreign matter is detected at the first sensor 59, the control unit 73 controls the driver 79 to close the tenth solenoid valve 57 and open the ninth solenoid valve 55. As a result, the sake of proper quality containing no foreign matter is provided through the outlet 49.

After providing sake, the control unit 73 controls the driver 79 to close the eighth solenoid valve 47 and open the seventh solenoid valve 45. As a result, sake lees are discharged from the fermenting tank 5 through the sake-lees discharge pipe 41.

The discharging of sake lees may manually be carried out by a worker observing information such as a message announcing a proper shipping time displayed on the display panel 83.

In this way, the first embodiment controls fermentation in the fermenting tank 5 according to detected capacitance changes, to produce quality sake in the material production unit 1. Capacitance detection by the embodiment never affects fermentation in the fermenting tank 5, and therefore, can properly produce sake of required quality.

Figure 10:
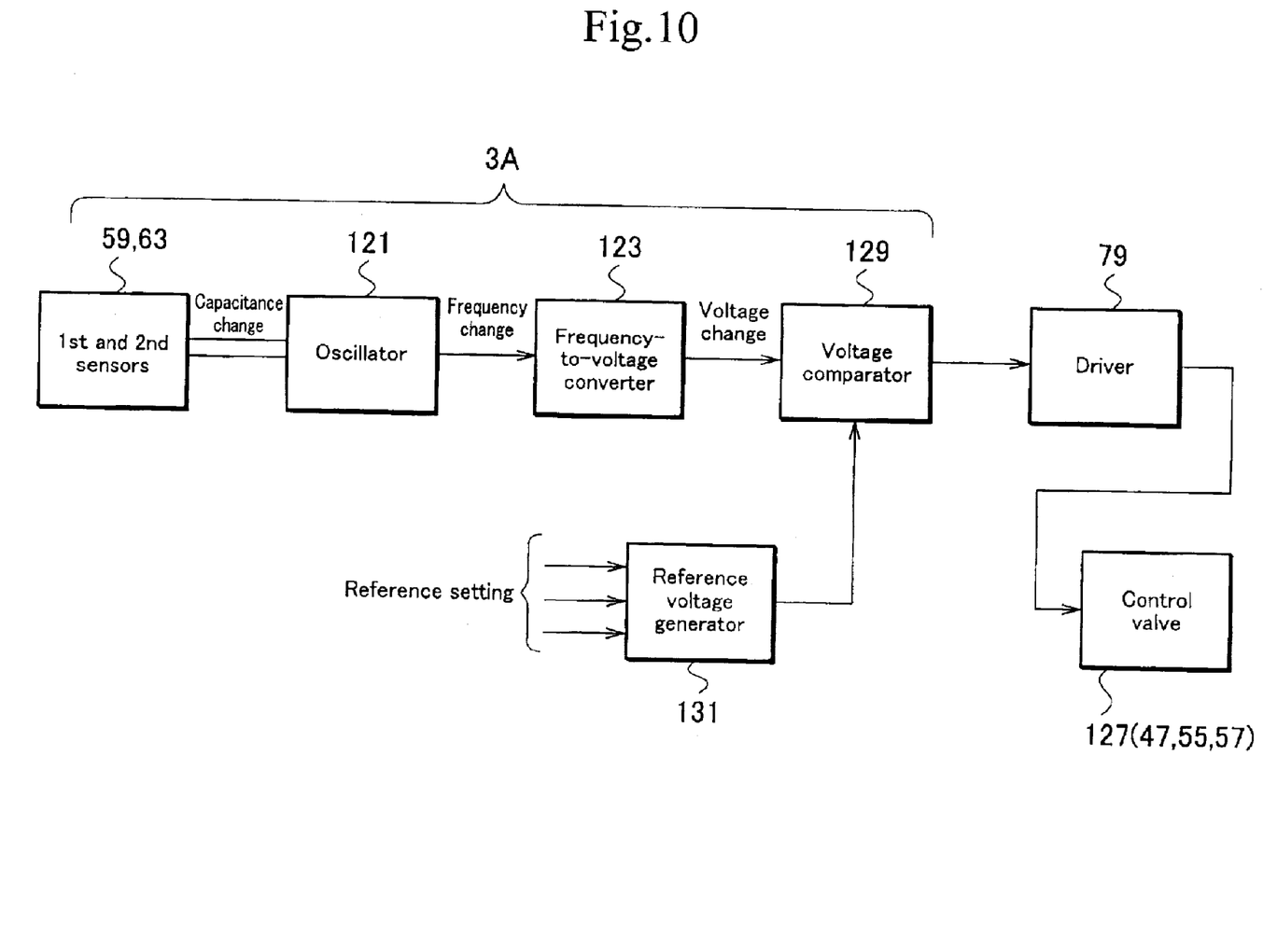
FIG. 10 is a block diagram showing a fermentation controller according to a modification of the first embodiment.

FIG. 10 shows a fermentation controller 3A according to a modification of the first embodiment. Components of FIG. 10 are basically the same as those of FIGS. 1 and 9, and the same components are represented with like reference numerals. The fermentation controller 3A of FIG. 10 employs a voltage comparator 129 and a reference voltage generator 131 in place of the A/D converter 125 and MPU 75 of FIG. 9.

The first and second sensors 59 and 63, oscillator 121, frequency-to-voltage converter 123, voltage comparator 129, and reference voltage generator 131 form the fermentation controller 3A.

The reference voltage generator 131 generates reference voltages used by the voltage comparator 129 for comparison. The reference voltages generated by the generator 131 include those corresponding to the no-foreign-matter capacitance change and production reference capacitance change mentioned above. The generator 131, therefore, serves as a reference storage unit.

The reference voltages generated by the reference voltage generator 131 are sent to the voltage comparator 129, which compares the reference voltages with a voltage representative of a detected capacitance change. According to the comparison result, the driver 79 is controlled to provide signals to the control valve 127 (47, 55, 57).

Like the first embodiment, the modification of FIG. 10 controls fermentation in the fermenting tank 5 according to a detected capacitance change, to produce quality sake in the material production unit 1. Capacitance detection by the modification never affects fermentation in the fermenting tank 5, and therefore, can properly produce sake of required quality.

In the above-mentioned embodiment and modification, the first and second sensors 59 and 63 are attached to the outlet pipe 43 and bypass pipe 65 that are linear. The cylinder 101, shield 105, and the like may be made of soft materials, so that the sensors 59 and 63 may easily be attached to bends and corners formed on the pipes 43 and 65. In this case, the spiral winding of the electrode 99 is advantageous in arranging the electrode 99 at a bend or corner.

The electrode 99 or 99A can directly be wound around any one of the bypass pipe 65 and outlet pipe 43 made of an insulator such as vinyl chloride and glass, to omit the cylinder 101. The cylinder 101 may be made as a part of the pipes 65 and 43. The first sensor 59 may be arranged inside the outlet pipe 43, and the second sensor 63 may be arranged inside the bypass pipe 65 or fermenting tank 5.

According to an embodiment of the present invention, capacitance values themselves instead of capacitance changes can be compared with the reference capacitance values.

The material to be produced with the fermentation controller of the present invention is not limited to sake. The material may be soy sauce, soybean paste, yogurt, vitamins, antibiotics, and other microbe-related materials. For example, for yogurt production, the present invention beforehand stores reference capacitance changes representative of reference lactic-acid levels for different quantities of base material and different numbers of ferment cells, and with the use of the reference capacitance changes and detected ones, properly produces yogurt of a lactic-acid level appropriate for shipment.

Comparing detected capacitance changes with reference ones according to the present invention is applicable to determine various kinds of shipment timing for a given material. The aim of the present invention, however, is not to determine appropriate shipment timing but is to control fermentation through the capacitance comparison.

What is claimed is:

1. A fermentation controller for controlling fermentation in a material production unit that produces a material by fermentation, comprising:

a capacitance sensor to detect a capacitance change representative of a fermenting state in the material production unit; and a storage unit to store a reference capacitance change representative of a reference fermenting state, a controller comparing the detected capacitance change with the reference capacitance change and controlling fermentation in the material production unit according to a comparison result, and the capacitance sensor including a measuring electrode and a ground electrode paired with one another for sensing capacitance in conjunction with one another, the around electrode being narrower than the measuring electrode and spaced from the measuring electrode, the paired measuring and around electrodes being spirally wound around a passage through which the fermenting material in the material production unit travels, the spiral of the paired measuring and ground electrodes being oriented in a traveling direction of the fermenting material.

* * * * *